United States Patent [19]

Davis et al.

[11] Patent Number: 5,460,805
[45] Date of Patent: Oct. 24, 1995

[54] BODY POWDER COMPRISING COLORANT

[75] Inventors: Robert A. Davis, Cottage Grove; Sheila M. Nichols, Richfield; Howard J. Buttery, Newport, all of Minn.

[73] Assignee: Minnesota Mining and Manufacturing Company, St. Paul, Minn.

[21] Appl. No.: 145,787

[22] Filed: Oct. 29, 1993

[51] Int. Cl.$^6$ .......................... A61K 7/021; A61K 7/035
[52] U.S. Cl. .............. 424/69; 424/63; 424/401; 424/489; 424/501
[58] Field of Search ................ 424/69, 401, 63, 424/489, 501

[56] References Cited

U.S. PATENT DOCUMENTS

| | | | |
|---|---|---|---|
| 4,665,107 | 5/1987 | Micale | 424/401 |
| 4,756,906 | 7/1988 | Sweeny | 424/63 |
| 4,879,174 | 11/1989 | Marabella | 424/401 |
| 4,879,175 | 11/1989 | Ugro, Jr. | 424/401 |
| 5,035,885 | 7/1991 | Arraudeau | 424/69 |
| 5,219,561 | 6/1993 | Gagnebien et al. | 424/401 |
| 5,234,711 | 8/1993 | Kamen et al. | 424/401 |

FOREIGN PATENT DOCUMENTS

| | | |
|---|---|---|
| 0210561 | 2/1987 | European Pat. Off. . |
| 0238225 | 9/1987 | European Pat. Off. . |
| 9106277 | 5/1991 | WIPO . |
| 9304660 | 3/1993 | WIPO . |

OTHER PUBLICATIONS

Search Report.

*Primary Examiner*—John C. Bleutge
*Assistant Examiner*—Amy Hulina
*Attorney, Agent, or Firm*—Gary L. Griswold; Walter N. Kirn; Dale A. Bjorkman

[57] ABSTRACT

Body powder is provided having microcapsules with a colorant located in or on the shell of said microcapsule. The microcapsules are present in an amount effective to impart color to the body powder when viewed in bulk and to substantially decrease in perceptible color upon rubbing said body powder on the skin.

16 Claims, No Drawings

BODY POWDER COMPRISING COLORANT

TECHNICAL FIELD

The present invention relates to body powders. More specifically, the present invention relates to body powders containing a colorant that is substantially more perceivable in bulk than after applied to the skin.

BACKGROUND OF THE INVENTION

Body powders have long been used for providing a cool, dry sensation to the skin. People use such powders for their moisture absorbing and sensation providing properties to treat sensitive or irritated skin or to prevent irritation of skin. Such powders are widely used as treatments for the diaper area of babies to prevent diaper rash, or to comfort the affected area where diaper rash is occurring. Similarly, many people use such body powders to soothe areas affected by a rash, or simply as an after-bath or shower treatment. Such powders may comprise talc, corn starch and additional additives such as perfumes, medicaments and the like.

Microcapsules have been used in the cosmetics industry to provide delivery in a dry form of fragrances, oils, emollients and the like.

U.S. Pat. No. 4,879,174 to Marabella discloses colorant sampler devices having microcapsules with colorant on their exterior surfaces that can transfer the colorant when the capsules contain liquids which wet the colorant.

U.S. Pat. No. 4,756,906 to Sweeny discloses cosmetic colorant compositions wherein the composition contains a first colorant and microcapsules in the composition contain a second colorant. Upon rupture of the microcapsules, the coloration of the second colorant is added to the composition, altering its color characteristics. This patent specifically discusses powder compositions at column 7, lines 39–42. The location of the second colorant is discussed at column 4, lines 9–30. In order to provide the greatest degree change in the overall color of the composition, it is preferred to have the second colorant located within the shell.

U.S. Pat. No. 5,035,885 to Arraudeau discloses powder for the care of the body and face containing synthetic thermoplastic material in the form of hollow microspheres.

SUMMARY OF THE INVENTION

Body powder is provided having microcapsules with a colorant located in or on the shell of said microcapsule. The microcapsules are present in an amount effective to impart color to the body powder when viewed in bulk and to substantially decrease in perceptible color upon rubbing said body powder on the skin.

DETAILED DESCRIPTION

Body powders are conventionally provided as a white or skin tone colored compositions. Skin-toned powders advantageously tend to blend in and do not impart an unnatural hue when applied to human skin. For general aesthetic purposes, however, it is desirable to be able to provide a body powder formulation in any color, but which formulation may be applied to the skin without imparting that alternative color in an unduly perceptible manner. The present invention provides such a formulation.

It has been surprisingly found that when one incorporates microcapsules having a colorant on the shell or in the shell of the microcapsule in a conventional body powder formulation, the color will be readily appreciated when the formulation is viewed in bulk (i.e. before application to the skin). On delivery of the body powder to the skin through a rubbing action, the perceived color of the body powder substantially decreases. While not being bound by theory, it is believed that the microcapsules break during this rubbing action and that the amount of colored material physically located where it can be seen is substantially decreased. This perceived color difference is apparent to the visual observer even though there is no actual reduction in mass of color-imparting material on the surface of the skin as compared to in the bulk composition.

In accordance with the present invention, microcapsules are prepared by in situ processes such as aminoplast polymerization. The techniques disclosed, generally referred to as an in situ polymerization reaction, yield for example, an aminoplast resin capsule wall material. In the process, a hydrophobic oil phase is dispersed in an aqueous phase containing the aminoplast resin precursors by applying high shear agitation. Addition of an acid catalyst initiates the polycondensation of the aminoplast precursors, resulting in the deposition of the aminoplast resin about the dispersed droplets of the oil phase, producing the microcapsules.

The hydrophobic inner phase for the capsule may be any in situ aminoplast encapsulatable composition as discussed in U.S. Pat. No. 3,516,941. The material or the dispersion produced by incorporation of the particulate may be fluid, semi-solid (e.g., gel), waxy or low melting (less than 100° C.) solid carrier phase. Typical materials may be fragrance oils, mineral oils, emollients such as isopropyl myristate, plasticizers such as the phthalate esters, waxes such as found in lipsticks, etc.

When the microcapsule is prepared by interfacial polycondensation, the capsule skin may be composed of any condensation polymer or addition polymer, e.g., polyamide, polyurethane, polysulfonamide, polyurea, polyester, polycarbonate, etc. Polyamides prepared by interfacial polycondensation of an amine with an acid chloride or polymers formed by reaction of isocyanate prepolymer with polyamines are preferred. Microcapsules formed by coacervation processes are also useful in forming microcapsule shells according to the present invention. Coacervation is the well known process of forming higher molecular weight gelatin polymers as taught in U.S. Pat. Nos. 5,800,458 and 2,800,457.

The capsules used in these constructions and generally in the practice of the present invention have average diameters between 4 and 100 microns. Preferably the average diameters are between 10 and 80 microns. The capsules preferably constitute from 2 to 60% by weight of the composition, and most preferably between 5 and 40% by weight of said composition.

The microcapsules contain a dye or pigment located at the outside of the shell or in the shell wall itself, as opposed to in the core of the microcapsule. This location of color-imparting aspect of the microcapsule is important to achieve maximum coloring effect on the bulk body powder formulation, while providing for effective reduction of the perceived color after application to the skin.

Any soluble dye may be used to make the compositions of this invention, provided it is safe for application to the skin, has a desirable color and is compatible with the other components of the composition. It is desirable to use a dye that it is approved for drug and cosmetic use (D&C dyes) or food, drug and cosmetic use (FD&C dyes). The preferred dyes for use in the compositions of this invention are water-soluble dyes. Appropriate dyes include FD&C Blue No. 1, FD&C Blue No. 2, FD&C Green No. 3, FD&C Red No. 3, FD&C Red No. 40, FD&C Yellow No. 5, FD&C Yellow No. 6, D&C Blue No. 4, D&C Blue No. 9, D&C Green No. 5, D&C Green No. 6, D&C Green No. 8, D&C Orange No. 4, D&C Orange No. 5, D&C Orange No. 10, D&C Orange No. 11, D&C Orange No. 17, FD&C Red No. 4, D&C Red No. 6, D&C Red No. 7, D&C Red No. 8, D&C Red No. 9, D&C Red No. 17, D&C Red No. 19, D&C Red No. 21, D&C Red No. 22, D&C Red No. 27, D&C Red No. 28, D&C Red No. 30, D&C Red No. 21, D&C Red No. 34, D&C Red No. 39, FD&C Red No. 40, D&C Violet No. 2, D&C Yellow No. 7, Ext. D&C Yellow No. 7, D&C Yellow No. 8, D&C Yellow No. 11, D&C Brown No. 1, Ext. D&C Violet No. 2, D&C Blue No. 6 and D&C Yellow No. 10. Such dyes are well known, commercially available materials, with their chemical structure being described, e.g., in 21 C.F.R. Part 74 (as revised Apr. 1, 1988) and the CTFA Cosmetic Ingredient Handbook, (1988), published by the Cosmetics, Toiletry and Fragrancy Association, Inc. Examples of additional suitable dyes include suitable water soluble dyes include Rhodamine B (Compound I in Table 1 below; bluish red with strong fluorescence; Color Index No. 45170), Tartrazine (II; yellow; described in JACS, 59 (1937) page 1501; Color Index No. 19140), Acid Yellow (III; reddish yellow; Color Index No. 18695), Acid Green (IV; green; Color Index No. 44025), Azure Blue. (V; greenish blue; made by condensing 0formylbenzenesulfonic acid with α-(N-ethylanilino)-m-toluenesulfonic acid, oxidine and convert the product formed into the sodium salt; Color Index No. 42090), Basic Green I (VI; bright green; Color Index No. 42040). Likewise, suitable oil soluble dyes include, for example, Sudan Red (VII; red; Color Index No. 26105). Additional dyes include flushed alkali blue, Nubian resin black, calco oil blue 2A, nigrosine black and the like.

The primary component of the body powder formulations of the present invention is of course the powders conventionally used in the preparation of this type of composition, such as talc, micas (natural or synthetic), starch (including corn, sago, rice, potato, corn, tapioca and the like), and the like and mixtures thereof.

The body powder composition may optionally comprise additional components conventional for use in standard formulations known in the art. For example, such additives such a perfumes, texture enhancers, non-microcapsule colorants or nacreous agents, deodorizers, and medicaments may additionally be incorporated.

The compositions of the present invention are prepared by making the microcapsules and the cosmetic compositions separately and then mixing the two under conditions which will not rupture a significant (e.g., greater than 5% or 10%) portion of the capsules, such as e.g. by gently sifting together. Preferably, fewer than 1% of the capsules will be broken during preparation of the final composition. The percentage of capsules and pigments in the composition can vary widely depending on the intensity of the desired effect, the optical intensity of the various pigments, and other aesthetic objectives. Generally, the microcapsules should comprise from 2-90% dry weight of the composition, preferably between 5 and 40% dry weight of the composition.

EXAMPLES

The following examples are provided for illustrative purposes, and are not to be construed as limiting the scope of the invention. Unless otherwise noted, all ratios and percentages of components described herein are by weight.

Example 1

Manufacture of colored microcapsules.

The following procedure was used to run a one liter encapsulation reaction using polymethylene urea chemistry to encapsulate mineral oil in a blue-red dyed shell.

| Precondensate recipe: | | |
|---|---|---|
| 37% formaldehyde - | 3739 gm | (A) |
| Urea - | 1190 gm | (B) |
| Melamine - | 210 gm | (C) |
| Buffer (K2B407) - | 12.3 gm | (D) |
| Water - | 6390 gm | (E) |

Combine charges A, B, C and D. Cook at 165° F. for 2.5 hours with mild stirring. Pour into charge E.

| Encapsulation charges: | | | |
|---|---|---|---|
| (A) | Precondensate - | 598 ml | |
| (B) | Added Water - | 18 ml | |
| (C) | Fill - | 184 ml | (Carnation Brand Mineral Oil-Witco Chemical Co.) |
| (D) | Sodium Sulfate - | 61.55 gm | |
| (E) | CMC 7L1 - | 1.48 gm | (Hercules) |
| (F) | FD & C Blue #1 - | 5.54 gm | |
| (G) | D & C Red #33 - | 0.78 gm | |
| (H) | Gluteraldehyde, 25% - | 6.16 | |

Procedure:

Charge A, B, F and G to a 1 liter baffled reactor.

Apply 2500 RPM with a Waring blender turbine and 70° F. and hold for 2–3 minutes to dissolve dyes. Slowly add D and E to the liquid vortex and hold for 10 minutes to insure solution. Add C and hold for 3–5 minutes to establish droplet size. Add H and maintain 2500 & 70° for an additional 3 minutes. Add 20% sulfuric acid dropwise to pH 3.2. Continue to stir at 70° for 3 hours at which-time add more acid to pH 2.0±0.1. Hold for 8 hours followed by a temperature increase to 140° F. Hold for 3 hours followed by a pH adjustment to 7.5. The intensely colored product may be filtered, washed and dried to obtain a free-flowing powder.

Example 2

Powders containing colored microcapsules.

A composition of 80% talc Fisher Scientific, lab grade and 20% microcapsules as described in Example 1 above were mixed until uniformly dispersed by shaking together in a glass jar.

Example 3

Powders containing colored microcapsules.

A composition of 50% talc Fisher Scientific, lab grade and 50% microcapsules as described in Example above were mixed until uniformly dispersed by shaking together in a glass jar.

Comparative Example 1

Powders containing non-microcapsule colorant.

A composition of 80% talc (Fisher Scientific, lab grade) and 20% Iron Oxide (a pigment commercially available from Pfizer, cosmetic grade 1599 HP) were mixed until uniformly dispersed by shaking together in a glass jar.

Comparative Example 2

Powders containing non-microcapsule colorant.

A composition of 50% talc (Fisher Scientific, lab grade) and 50% Iron Oxide (a pigment commercially available from Pfizer, cosmetic grade 1599 HP) were mixed until uniformly dispersed by shaking together in a glass jar.

Determination of Standardized Color Loss (SCL)

Evaluation of the coloring effect of microcapsules in body powders and perceived disappearance of same was carried out using CIELAB coordinates measured by means of a Hunter Labscan colorimeter. The colorimeter was adjusted to the following settings.

10 degree viewer
D65 illuminant
1/2 inch diameter viewing aperture
UV filter

The instrument was then calibrated to zero reflectance with a black tile and 100% reflectance with a white tile.

The perceived color difference of the microcapsule-containing body powder as compared to the same body powder not containing microcapsules was determined both in bulk and after application to the skin of a caucasian male. Both the control body powder (no microcapsules) and the colored body powder were evaluated according to the following procedure. The powder was provided in bulk as a 2.0 gram sample in a 2.15cm³ 0.3cm thick container, and inserted into the light source of the instrument. A white tile was then placed over the sample and the CIELAB data was obtained from the colorimeter. The color difference ($\Delta E^*ab$) of each test sample was calculated according to the following equation:

$$\Delta E^*ab = \sqrt{(\Delta L^*)^2 + (\Delta b^*)^2}$$

where delta E*ab represents the difference in color between the control body powder and the colored body powder, and delta L*, delta a*, and delta b* terms are the color coordinates. The delta L* term represents the lightness of the color, the delta a* term represents the redness or greenness of the color, and the delta b* term represents the yellowness or blueness of the color. For a further discussion see "Principles of Color Technology" second Ed , F W. Billmeyer and M. Saltzmann, pages 59 through 60 and 102 through 104.

For evaluation of the color of the body powder after being rubbed on the skin, a 0.06 gram sample was rubbed onto a 19cm² area of the back of the hand of a male caucasian, and CIELAB coordinates were measured as described above. The $\Delta E^*ab$ of body powders were determined by comparing CIELAB coordinates of body powder not containing microcapsules with those of body powder containing microcapsules. A Standardized Color Loss (SCL) is determined by subtracting the $\Delta E^*ab$ of body powder after being rubbed on the skin of a caucasian male having Lab values of about 46, 6 and 13, respectively from the $\Delta E^*ab$ of the body powder in bulk. Thus, $$SCL = \Delta E^*ab_{bulk} - \Delta E^*ab_{skin}.$$

Data produced by the above methodology is reported Table 1 below.

TABLE 1

| Material | Sample Format | L | a | b | L Std Dev | a Std Dev | b Std Dev | ΔE |
|---|---|---|---|---|---|---|---|---|
| Talc | Bulk | 87.67 | −0.79 | 1.83 | 0.18 | 0.02 | 0.04 | |
| Example 2 | Bulk | 69.47 | −7.10 | −12.25 | 0.42 | 0.17 | 0.43 | 23.86 |
| Example 3 | Bulk | 53.09 | −9.48 | −22.56 | 0.20 | 0.05 | 0.13 | 43.199 |
| Comparative Example 1 | Bulk | 65.04 | 10.55 | 7.25 | 0.06 | 0.01 | 0.02 | 25.886 |
| Comparative Example 2 | Bulk | 49.90 | 15.76 | 10.47 | 0.11 | 0.05 | 0.03 | 42.132 |
| Skin-washed | | 46.23 | 5.67 | 13.27 | 0.81 | 0.87 | 0.02 | |
| Example 2 | on skin | 61.86 | 1.31 | 2.81 | 0.63 | 0.57 | 0.92 | 3.3487 |
| Example 3 | on skin | 47.20 | −5.71 | −7.11 | 2.10 | 1.55 | 3.70 | 22.363 |
| Comparative Example 1 | on skin | 49.23 | 4.37 | 11.77 | 1.81 | 0.81 | 0.46 | 17.336 |
| Comparative Example 1 | on skin | 40.32 | 21.70 | 14.31 | 1.37 | 0.74 | 0.05 | 32.729 (avg. of both = 25.03) |
| Comparative Example 2 | on skin | 35.61 | 20.19 | 12.56 | 0.18 | 1.31 | 0.50 | 35.139 |
| Mean Talc on Skin | | 64.71 | 2.34 | 4.235 | 2.04 | 0.365 | 0.625 | |

The measurements of comparative Example 1 on the skin were repeated because the high amount of color noted on rubbing the composition on the skin was believed to be the result of incomplete mixing.

As can be seen from calculation of the SCL values for Examples 2, 3 and Comparative Examples 1 and 2 as reported in Table 2, incorporation of microcapsules in body powders provides a significant coloring effect of the powder in bulk, yet allows application of the powder to the skin with resultant substantial reduction of the perceived color of the powder once resident on the skin. By adjusting the level of microcapsule content in the body powder, the perceived color imparted to the skin may be varied from a substantial reduction (toning down the perceived color) to almost complete disappearance of the color.

TABLE 2

| | Δ E Bulk | Δ E On Skin |
|---|---|---|
| 1 | 23.86 >> | 3.34 |
| 2 | 43.19 >> | 22.36 |
| 3 | 25.88 > | 25.03 |
| 4 | 42.13 > | 35.13 |

The decrease in color of the body powder when applied to the skin is considered to be substantial when the intensity of the color is decreased by more than about one-half of its bulk color intensity. Preferably, more about ⅓ of its bulk color intensity, and, more preferably, about ¼ of its bulk color intensity.

Preferably, the SCL value is greater than 10 and more preferably greater than 15. Additionally, it is most desirable to have $\Delta E^*ab_{skin}$ be less than 8, more preferably less than 5 and most preferably less than 4.

What is claimed:

1. Body powder for application to skin comprising microcapsules having a colorant located in or on the shell wall of said microcapsule, said microcapsules being present in an amount effective to impart the color of said colorant to the body powder when viewed in bulk and to substantially decrease in perceptible color of said colorant upon rubbing said body powder on the skin.

2. The powder of claim 1, wherein said microcapsules are 2 to 60% by weight of the body powder.

3. The powder of claim 1, wherein said microcapsules are 5 to 40% by weight of the body powder.

4. The powder of claim 1, wherein the predominant non-microcapsule component of said powder is talc.

5. The powder of claim 1, wherein the predominant non-microcapsule component of said powder is natural or synthetic mica.

6. The powder of claim 1, wherein the predominant non-microcapsule component of said powder is starch.

7. The powder of claim 6, wherein said starch is selected from the group consisting of corn, sago, rice, potato, corn and tapioca starches.

8. The powder of claim 6, wherein said starch is corn starch.

9. The powder of claim 1, wherein the microcapsules are aminoplast resin microcapsules.

10. The powder of claim 1, wherein the microcapsule is prepared by interfacial polycondensation.

11. The powder of claim 1, wherein the microcapsule is prepared by a coacervation process.

12. The powder of claim 1, said powder having an SCL value greater than 10.

13. The powder of claim 1, said powder having an SCL value greater than 15.

14. The powder of claim 1, said powder having a $\Delta E^*ab_{skin}$ less than 20.

15. The powder of claim 1, said powder having a $\Delta E^*ab_{skin}$ less than 5.

16. The powder of claim 1, said powder having a $\Delta E^*ab_{skin}$ less than 4.

* * * * *

UNITED STATES PATENT AND TRADEMARK OFFICE
CERTIFICATE OF CORRECTION

PATENT NO. : 5,460,805
DATED : 10-24-95
INVENTOR(S) : Robert A. Davis, Sheila M. Nichols and Howard J. Buttery It is certified that error appears in the above-indentified patent and that said Letters Patent is hereby corrected as shown below:

Column 4, Line 57, After "Example" insert --1--. (PTO error)

Column 5, Line 52-53, delete the formula: " $\Delta E^*ab = \sqrt{[(\Delta L^*)^2 + (\Delta b^*)^2]}$ " and insert the formula -- $\Delta E^*ab = \sqrt{[(\Delta L^*)^2 + (\Delta a^*)^2 + (\Delta b^*)^2]}$ -- therefore. (PTO error)

Column 7, Line 21, after the word "potato" delete the word "corn". (3M error)

Signed and Sealed this

Tenth Day of June, 1997

*Attest:*

BRUCE LEHMAN

*Attesting Officer*     Commissioner of Patents and Trademarks